US009707715B2

(12) United States Patent
Shawver et al.

(10) Patent No.: US 9,707,715 B2
(45) Date of Patent: Jul. 18, 2017

(54) ELASTOMERIC ARTICLES HAVING A WELDED SEAM MADE FROM A MULTI-LAYER FILM

(75) Inventors: Susan Elaine Shawver, Roswell, GA (US); Martin S. Shamis, Alpharetta, GA (US); Alphonse Carl DeMarco, Greenville, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 968 days.

(21) Appl. No.: 13/285,879

(22) Filed: Oct. 31, 2011

(65) Prior Publication Data

US 2013/0104286 A1 May 2, 2013

(51) Int. Cl.
*A41D 19/00* (2006.01)
*B29C 65/74* (2006.01)
(Continued)

(52) U.S. Cl.
CPC ...... *B29C 65/7441* (2013.01); *A41D 19/0006* (2013.01); *A41D 19/0055* (2013.01); *A41D 19/0068* (2013.01); *A41D 19/01558* (2013.01); *A41D 27/245* (2013.01); *A61B 42/00* (2016.02); *B29C 65/02* (2013.01); *B29C 66/1122* (2013.01); *B29C 66/244* (2013.01); *B29C 66/43* (2013.01); *B29C 66/71* (2013.01); *B29C 66/723* (2013.01); *B29C 66/8322* (2013.01); *A61B 2017/00526* (2013.01); *A61B 2017/00849* (2013.01); *A61B 2017/00907* (2013.01); *B29C 65/08* (2013.01); *B29C 65/222* (2013.01); *B29C 65/7443* (2013.01); *B29C 66/7294* (2013.01); *B29C 66/73152* (2013.01);
(Continued)

(58) Field of Classification Search
CPC ............ A41D 19/0068; A41D 19/0006; A41D 19/0058; A41D 19/01558; A41D 19/0055; A41D 19/0082; A41D 19/01547; A41D 27/245; A41D 2300/52; A41D 31/0061; B29L 2031/4864; A61B 19/04
USPC ....... 2/159, 161.3, 161.6, 161.7, 161.8, 164, 2/167–169; 428/212, 213, 215, 216
See application file for complete search history.

(56) References Cited

U.S. PATENT DOCUMENTS 1,855,809 A 4/1932 Sheppard et al.
2,810,161 A 10/1957 Milton, Jr.
(Continued)

FOREIGN PATENT DOCUMENTS

DE 10014095 A1 9/2001
EP 0350562 A2 1/1990
(Continued)

OTHER PUBLICATIONS

Citation of Patent Applications.
(Continued)

*Primary Examiner* — Jameson Collier
(74) *Attorney, Agent, or Firm* — Dority & Manning, P.A.

(57) ABSTRACT

Elastomeric articles, such as gloves, are made by welding together two plies of a multi-layer film. The film plies are welded together through ultrasonic bonding, thermal bonding, or mixtures thereof. The multi-layer film includes at least three layers that, in one embodiment, are coextruded. Each layer of the multi-layer film is made from a different composition that produces layers having different properties.

17 Claims, 4 Drawing Sheets

(51) Int. Cl.
| | | |
|---|---|---|
| *A41D 19/015* | (2006.01) | |
| *A41D 27/24* | (2006.01) | |
| *B29C 65/00* | (2006.01) | |
| *B29C 65/02* | (2006.01) | |
| *A61B 42/00* | (2016.01) | |
| *A61B 17/00* | (2006.01) | |
| *B29L 31/48* | (2006.01) | |
| *B29C 65/08* | (2006.01) | |
| *B29C 65/22* | (2006.01) | |

(52) U.S. Cl.
CPC .... *B29C 66/8242* (2013.01); *B29K 2995/007* (2013.01); *B29L 2031/4864* (2013.01)

(56) References Cited

U.S. PATENT DOCUMENTS

| | | | |
|---|---|---|---|
| 3,124,807 A | 3/1964 | Frenkel et al. | |
| 3,268,433 A | 8/1966 | Abere | |
| 3,281,498 A | 10/1966 | Watkins et al. | |
| 3,866,245 A | 2/1975 | Sutherland | |
| 3,870,150 A | 3/1975 | Hummel | |
| 4,034,853 A | 7/1977 | Smith | |
| 4,205,028 A | 5/1980 | Brueggemann et al. | |
| 4,430,759 A | 2/1984 | Jackrel | |
| 4,434,126 A | 2/1984 | McGary, Jr. et al. | |
| 4,463,156 A | 7/1984 | McGary, Jr. et al. | |
| 4,476,588 A | 10/1984 | Long | |
| 4,643,791 A | 2/1987 | Jurrius et al. | |
| 4,660,228 A | 4/1987 | Ogawa et al. | |
| 4,677,697 A | 7/1987 | Hayes | |
| 4,679,257 A * | 7/1987 | Town | 2/164 |
| 4,745,635 A | 5/1988 | Kinnear | |
| 4,804,432 A | 2/1989 | Jurrius et al. | |
| 4,865,903 A * | 9/1989 | Adiletta | 428/215 |
| 4,918,755 A | 4/1990 | Kinnear | |
| 4,921,672 A | 5/1990 | Bock | |
| 4,928,322 A * | 5/1990 | Bradfield | 2/169 |
| 5,014,361 A * | 5/1991 | Gray | 2/167 |
| 5,093,422 A | 3/1992 | Himes | |
| 5,451,439 A | 9/1995 | Bigg | |
| 5,548,125 A | 8/1996 | Sandbank | |
| 5,640,720 A | 6/1997 | Sandbank | |
| 5,644,798 A | 7/1997 | Shah | |
| 5,679,423 A | 10/1997 | Shah | |
| 5,682,613 A * | 11/1997 | Dinatale | 2/168 |
| 5,851,683 A | 12/1998 | Plamthottam et al. | |
| 5,966,741 A | 10/1999 | Klecina | |
| 5,997,676 A | 12/1999 | Jurrius et al. | |
| 5,998,540 A * | 12/1999 | Lipkin et al. | 524/591 |
| 6,017,997 A | 1/2000 | Snow et al. | |
| 6,021,524 A | 2/2000 | Wu et al. | |
| 6,039,829 A | 3/2000 | French | |
| 6,243,875 B1 | 6/2001 | French | |
| 6,286,144 B1 * | 9/2001 | Henderson et al. | 2/69 |
| 6,298,491 B1 | 10/2001 | Blustin et al. | |
| 6,360,373 B1 * | 3/2002 | Rehn et al. | 2/161.6 |
| 6,378,137 B1 | 4/2002 | Hassan et al. | |
| 6,425,136 B1 | 7/2002 | Schlamp et al. | |
| 6,514,572 B1 | 2/2003 | Koonce et al. | |
| 6,602,452 B2 | 8/2003 | Schuessler | |
| 6,637,035 B1 | 10/2003 | Brinkmann et al. | |
| 6,641,879 B1 | 11/2003 | Matsuura et al. | |
| 6,673,871 B2 | 1/2004 | Warneke et al. | |
| 6,720,049 B2 | 4/2004 | DiMaio | |
| 6,748,605 B1 | 6/2004 | Brinkmann | |
| 6,895,600 B2 | 5/2005 | Williams | |
| 7,052,642 B2 * | 5/2006 | Triebes et al. | 264/305 |
| 7,178,171 B2 * | 2/2007 | Griesbach, III | 2/161.7 |
| 7,294,678 B2 | 11/2007 | McGlothlin et al. | |
| 7,329,442 B2 * | 2/2008 | Modha et al. | 428/35.7 |
| 7,504,145 B2 | 3/2009 | Vance et al. | |
| 7,624,456 B2 * | 12/2009 | Williams et al. | 2/169 |
| 7,922,854 B2 | 4/2011 | Sabbagh et al. | |
| 8,256,030 B2 * | 9/2012 | Williams et al. | 2/169 |
| 8,566,965 B2 * | 10/2013 | Shamis et al. | 2/167 |
| 8,769,722 B2 * | 7/2014 | Williams et al. | 2/169 |
| 2001/0051481 A1 | 12/2001 | Carroll | |
| 2002/0010957 A1 | 1/2002 | Katz | |
| 2005/0070682 A1 | 3/2005 | Lawrey | |
| 2006/0117457 A1 * | 6/2006 | Williams et al. | 2/164 |
| 2006/0143767 A1 | 7/2006 | Yang et al. | |
| 2007/0104904 A1 | 5/2007 | Hamann et al. | |
| 2007/0112137 A1 | 5/2007 | Niemark | |
| 2007/0124849 A1 * | 6/2007 | Williams et al. | 2/275 |
| 2007/0134303 A1 | 6/2007 | Yahiaoui et al. | |
| 2007/0220653 A1 * | 9/2007 | Mack et al. | 2/159 |
| 2007/0240249 A1 | 10/2007 | Poirier et al. | |
| 2008/0076315 A1 | 3/2008 | McCormack et al. | |
| 2008/0102093 A1 * | 5/2008 | Close et al. | 424/402 |
| 2008/0103460 A1 * | 5/2008 | Close et al. | 604/292 |
| 2008/0120761 A1 * | 5/2008 | Yang et al. | 2/167 |
| 2010/0008957 A1 * | 1/2010 | Mundschau et al. | 424/401 |
| 2012/0054943 A1 | 3/2012 | Tao | |
| 2013/0067637 A1 * | 3/2013 | Lin et al. | 2/167 |

FOREIGN PATENT DOCUMENTS

| | | |
|---|---|---|
| FR | 1555846 | 12/1967 |
| GB | 2164540 A | 3/1986 |
| GB | 2264632 A | 3/1993 |
| JP | 61-62540 | 3/1986 |
| JP | 61-289102 | 12/1986 |
| JP | 02-139401 | 5/1990 |
| JP | 9-137310 | 5/1997 |
| JP | 11-140715 | 5/1999 |
| JP | 2000-175938 | 6/2000 |
| JP | 2000-355809 | 12/2000 |
| JP | 2002-317320 | 10/2002 |
| JP | 2005-163193 | 6/2005 |
| JP | 2006-118073 | 5/2006 |
| JP | 2008-303286 | 12/2008 |
| JP | 11-105888 | 4/2011 |
| WO | WO 00/07671 | 2/2000 |
| WO | WO 01/00408 | 1/2001 |
| WO | WO 2011/127259 | 10/2011 |

OTHER PUBLICATIONS

Double Layers, Glove Making Machine; Alibaba.com; date unknown.
Food Disposable Glove Making Machine; Alibaba.com; date unknown.
Glove Machine; Alibaba.com; date unknown.
PE Glove Machine; Alibaba.com; date unknown.
PE Film Glove Making Machine; Alibaba.com; date unknown.
PE Glove Making Machine; Alibaba.com; date unknown.
Disposable Long Sleeve Glove Making Machine; Alibaba.com; date unknown.
International Search Report for PCT/IB2012/055122; dated Feb. 1, 2013.
Kraton® G1652 E Polymer Data Document; May 13, 2011.
U.S. Appl. No. 13/285,951, filed Oct. 31, 2011, Shamis et al., Elastomeric Articles Having a Welded Seam that Possess Strength and Elasticity.

* cited by examiner

ELASTOMERIC ARTICLES HAVING A WELDED SEAM MADE FROM A MULTI-LAYER FILM

BACKGROUND

Elastomeric articles made from natural or synthetic rubber are used in many different applications including being used as surgeon gloves, examination gloves, prophylactics, catheters, balloons, tubing, and the like. Elastomeric materials have been useful in the production of such articles because of their physical properties. For example, the materials not only can be stretched, but are also capable of substantially returning to their original shape when released.

Traditionally, elastomeric articles have been manufactured through the use of a mold or former in the shape of the final article to be produced. For example, when manufacturing a glove, a hand-shaped mold or former is first dipped in a coagulant slurry. After the slurry has dried on the former, the former is dipped in a rubber-type material, such as a natural or synthetic latex. The former may be dipped several times into the rubber material in order to build up a layer on the former of the desired thickness. The formed elastomeric article is then cured, cooled and stripped from the mold.

Multi-step dipping processes as described above can produce elastomeric articles, such as gloves, that are elastic, are form-fitting, have tactile sensitivity, and are chemically resistant. Unfortunately, however, the above described multi-step dipping process is both labor and energy intensive. Further, only certain types of rubber materials are amenable to the dipping process.

In an alternative embodiment, instead of producing gloves through a dipping process, gloves can also be produced by heat sealing together two layers of film. Forming a glove through a heat sealing process can be relatively less expensive. Unfortunately, however, problems have been experienced in the past in being able to produce heat sealed gloves that have elastic properties that provide tactile sensitivity. In this regard, the gloves typically do not have form-fitting properties, are typically made from a thicker film than dipped products, and are oversized in relation to a hand resulting in a poor fit.

In view of the above, improvements are needed in producing form-fitting gloves with excellent tactile sensitivity in a more cost-effective manner.

SUMMARY

In general, the present disclosure is directed to an elastic article, such as a glove, made from a thermoplastic elastomer film. In one embodiment, the film comprises a multi-layer film. The multi-layer film may comprise, for instance, a co-extruded film. In accordance with the present disclosure, the film includes multiple layers having different characteristics. Once the film is formed, the film is then used to produce elastic articles, such as gloves, by welding at least two pieces of the film together. For example, a first hand-shaped panel made from a multi-layer film may be welded to a second hand-shaped panel also made from the film about their peripheries in order to form a glove. The elastomeric material used to form the film is selected so that the material can thermally or ultrasonically bond to itself. Thus, the first hand-shaped panel can be attached to the second hand-shaped panel without the use of an adhesive.

In the manner described above, gloves and other elastic articles can be produced without having to dip a former into multiple dipping solutions in order to form the article.

In one embodiment, for instance, the present disclosure is directed to a glove having form-fitting properties when worn by a user. The glove includes a first hand-shaped panel welded to a second hand-shaped panel about their peripheries or outer perimeters. The two panels are welded together leaving a hollow opening for receiving a hand. In accordance with the present disclosure, the hand-shaped panels are comprised of an elastic multi-layer film.

The multi-layer film comprises at least one middle layer positioned in between a first layer and a second layer. The first layer can form or at least face an exterior surface of the glove. The second layer forms or faces an interior surface of the glove. Each of the layers may contain a thermoplastic elastomer. Each layer may be formed from a different composition of materials. The second layer, in one embodiment, contains a friction-reducing additive for facilitating donning of the glove. The friction-reducing additive may comprise, for instance, particles including nanoparticles. The particles may comprise, for instance, a filler such as silicon dioxide and/or aluminum oxide. The friction-reducing additive may also comprise polymer particles or a polymeric additive. The friction-reducing additive may be incorporated into the second layer or may be applied to a surface of the second layer. In one embodiment, for instance, the friction-reducing additive may comprise an oil, such as a silicone oil applied to the surface of the second layer. The multi-layer film can have a thickness of from about 0.5 mil to about 8 mil, such as from about 1 mil to about 6 mil.

In accordance with the present disclosure, the multi-layer film may comprise a non-laminated film. In particular, the multi-layer film can be made in-line whereas all the layers of the film are formed at once as opposed to attaching separate film plies together. For example, the film may be coextruded.

In one embodiment, all three layers of the multi-layer film contain the same thermoplastic elastomer. For instance, in one embodiment, the three layers of the film are primarily made from a thermoplastic polyurethane elastomer. The thermoplastic polyurethane elastomer may be polyether based or polyester based. Although each layer contains the thermoplastic elastomer, each layer can include different ingredients and components. For example, as described above, the second layer can contain a friction-reducing additive. In one embodiment, the first layer may contain an additive that enhances gripping or reduces blocking, and/or a coloring agent.

In an alternative embodiment, at least two layers of the multi-layer film, such as all three layers may be made from a different thermoplastic elastomer.

Other features and aspects of the present disclosure are discussed in greater detail below.

BRIEF DESCRIPTION OF THE DRAWINGS

A full and enabling disclosure of the present invention, including the best mode thereof to one skilled in the art, is set forth more particularly in the remainder of the specification, including reference to the accompanying figures, in which.

Figure 1A:
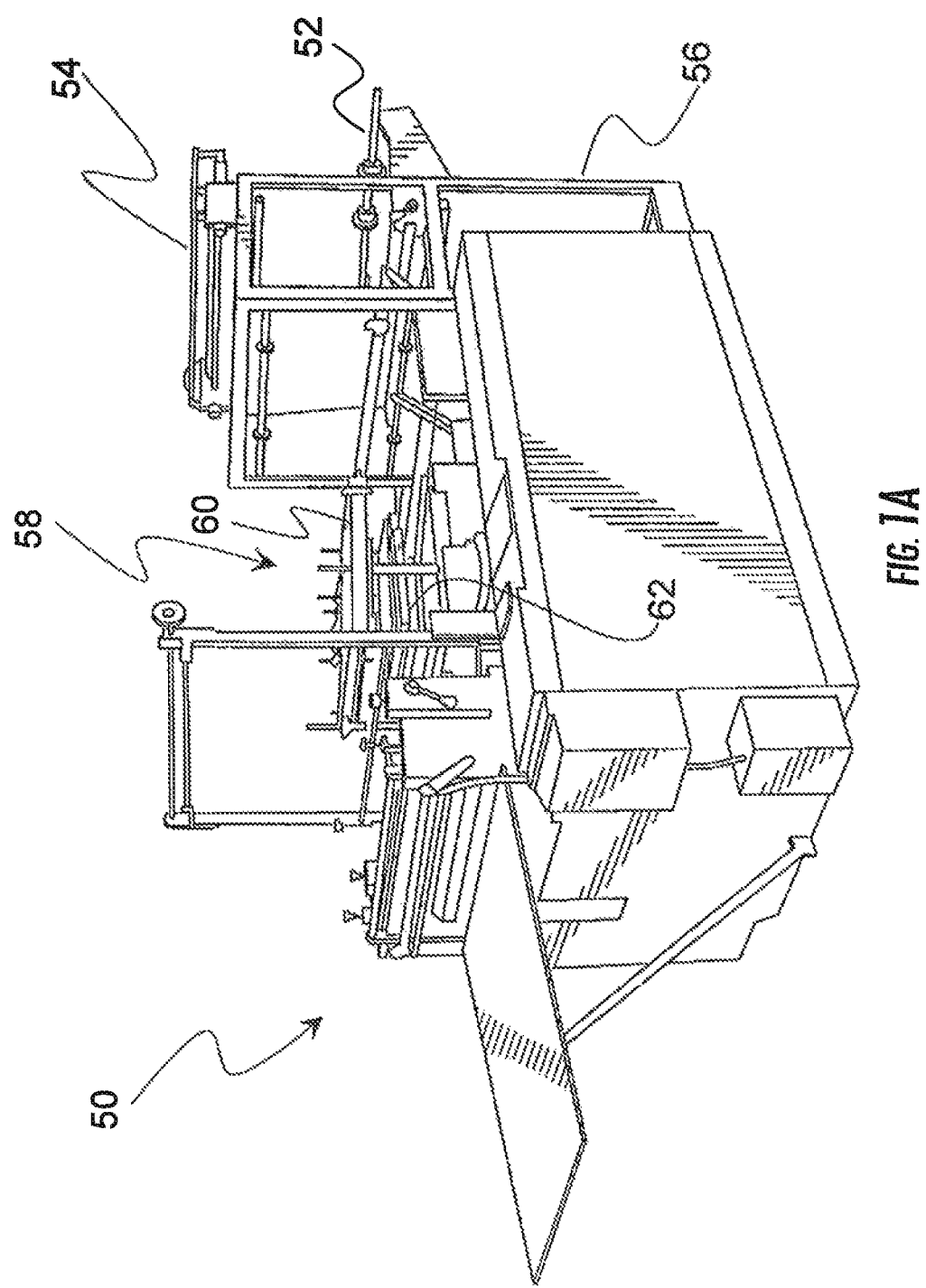
FIG. 1A is a perspective view of one embodiment of a process for making gloves in accordance with the present disclosure.

Repeat use of reference characters in the present specification and drawings is intended to represent the same or analogous features or elements of the present invention.

Definitions

As used herein, the term "elastomeric" and "elastic" and refers to a material that, upon application of a stretching force, is stretchable in at least one direction (such as the CD direction), and which upon release of the stretching force, contracts/returns to approximately its original dimension. For example, a stretched material may have a stretched length that is at least 50% greater than its relaxed unstretched length, and which will recover to within at least 50% of its stretched length upon release of the stretching force. A hypothetical example would be a one (1) inch sample of a material that is stretchable to at least 1.50 inches and which, upon release of the stretching force, will recover to a length of not more than 1.25 inches. Desirably, the material contracts or recovers at least 50%, and even more desirably, at least 80% of the stretched length.

As used herein the terms "extensible" or "extensibility" generally refers to a material that stretches or extends in the direction of an applied force by at least about 50% of its relaxed length or width. An extensible material does not necessarily have recovery properties. For example, an elastomeric material is an extensible material having recovery properties.

As used herein, the term "percent stretch" refers to the degree to which a material stretches in a given direction when subjected to a certain force. In particular, percent stretch is determined by measuring the increase in length of the material in the stretched dimension, dividing that value by the original dimension of the material, and then multiplying by 100. Specifically, the test uses two clamps, each having two jaws with each jaw having a facing in contact with the sample. The clamps hold the material in the same plane, usually vertically, separated by 2 inches and move apart at a specified rate of extension. The samples have a width of 2 inches and a length of 7 inches. The jaw facing height is 1 inch and width is 3 inches, with a constant rate of extension of 300 mm/min, The specimen is clamped in, for example, a Sintech 2/S tester with a Renew MTS mongoose box (control) and using TESTWORKS 4.07b software (Sintech Corp, of Cary, N.C.).

The test is conducted under ambient conditions. Results are generally reported as an average of three specimens and may be performed with the specimen in the cross direction (CD) and/or the machine direction (MD).

As used herein, the term "set" refers to retained elongation in a material sample following the elongation and recovery, i.e., after the material has been stretched and allowed to relax during a cycle test.

As used herein, the term "percent set" is the measure of the amount of the material stretched from its original length after being cycled (the immediate deformation following the cycle test). The percent set is where the retraction curve of a cycle crosses the elongation axis. The remaining strain after the removal of the applied stress (zero load) is measured as the percent set.

As used herein, the "hysteresis loss" of a sample may be determined by first elongating the sample ("load up") and then allowing the sample to retract ("load down"). The hysteresis loss is the loss of energy during this cyclic loading. The hysteresis loss is measured as a percentage. As used herein, the percent set and hysteresis loss are determined based on stretching a sample to 250% elongation and then allowing the sample to relax. The sample sizes for percent set and hysteresis loss are a width of 2 inches and a length of 7 inches. The same equipment and setup as described in determining percent stretch may be used to determine percent set and hysteresis loss.

As used herein, the term "weld" refers to securing at least a portion of a first polymer film with a portion of at least a second polymer film by temporarily rendering at least a portion of one film or an intermediate material into a softened or plastic state and joining the films without the use of mechanical attachments such as, for instance, stitching or without the use of an adhesive material that causes the films to stick together. Two or more films can be welded together in various ways such as through thermal bonding, ultrasonic bonding, pressure bonding, solvent bonding, or mixtures thereof.

As used herein, a "friction-reducing additive" refers to any material or composition incorporated into a layer or applied to a surface of a layer that reduces the static coefficient of friction. As used herein, the static coefficient of friction is measured according to ASTM Test D1894-11.

As used herein, an "elastomer" refers to any polymer material that is elastomeric or elastic and includes plastomers.

As used herein, the tensile properties of a film including modulus and load at break are measured according to ASTM Test D412-06 using Die D.

As used herein, a layer that is formed from a "different composition of materials" in relation to another layer refers to any formulation variation between the two layers. Two layers having a different composition of materials may include layers made from different thermoplastic elastomers or may include layers containing different additives or the same additives in different amounts. Two layers being made from a different composition of materials can also occur when the color of each layer is different.

DETAILED DESCRIPTION

It is to be understood by one of ordinary skill in the art that the present discussion is a description of exemplary embodiments only, and is not intended as limiting the broader aspects of the present disclosure.

In general, the present disclosure is directed to elastic articles made from a multi-layer film and is directed to a method for making the elastic articles. As opposed to being produced via a multi-step dipping process which is both labor and energy intensive, elastic articles of the present disclosure are produced by welding at least two pieces of film together. For instance, in one embodiment, a glove is formed by welding two hand-shaped panels together which are both made from the multi-layer film. In accordance with the present disclosure, thermoplastic elastomers are selected for use in making the multi-layer films that produce elastic articles, such as gloves, that provide form-fitting properties. In particular, gloves made according to the present disclosure provide comfort, tactile sensitivity, chemical resistance, and physical property performance.

When forming gloves from a multi-step dipping process, only particular types of polymers may be used due to the manner in which the gloves are formed. According to the present disclosure, however, any thermoplastic elastomer may be used to form the multi-layer film as long as the polymer is capable of being formed into a film and bonding to itself. The film, for instance, may comprise a cast film or a blown film. Thermoplastic elastomers that may be formed into films and used to form gloves in accordance with the present disclosure include polyurethanes, polyolefins, styrenic block copolymers, polyether amides, and polyesters. Of particular advantage, an appropriate thermoplastic elastomer may be selected depending upon the physical properties that are desired. In particular, a thermoplastic elastomer can be selected that is tailored for a given end use or application.

In one embodiment, a thermoplastic elastomer may be used to form the elastic article that contains a weld-enhancing additive that allows or enhances the ability of a thermoplastic elastomer to bond to itself. A weld-enhancing additive, for instance, may comprise low-melting temperature particles or other ingredients that promote easier welding.

Films made according to the present disclosure generally include multiple layers wherein each layer has different physical properties and/or a different composition of materials. One layer of the film, for instance, can be constructed so as to provide easy donning of a glove made from the film. An opposite layer of the film, on the other hand, may be formulated to provide tactile sensitivity and grip performance. One of the layers can also include a coloring agent for improving the aesthetic appeal of the glove.

In one particular embodiment, a glove can be made in accordance with the present disclosure made from a film that includes at least three layers. The three layers can be coextruded so that multiple films do not have to be laminated together to produce the elastic article. In other words, although the film includes at least three layers, the multi-layer film comprises a single ply and may be referred to as a composite film as opposed to combining together multiple sheets of film.

Figure 2:
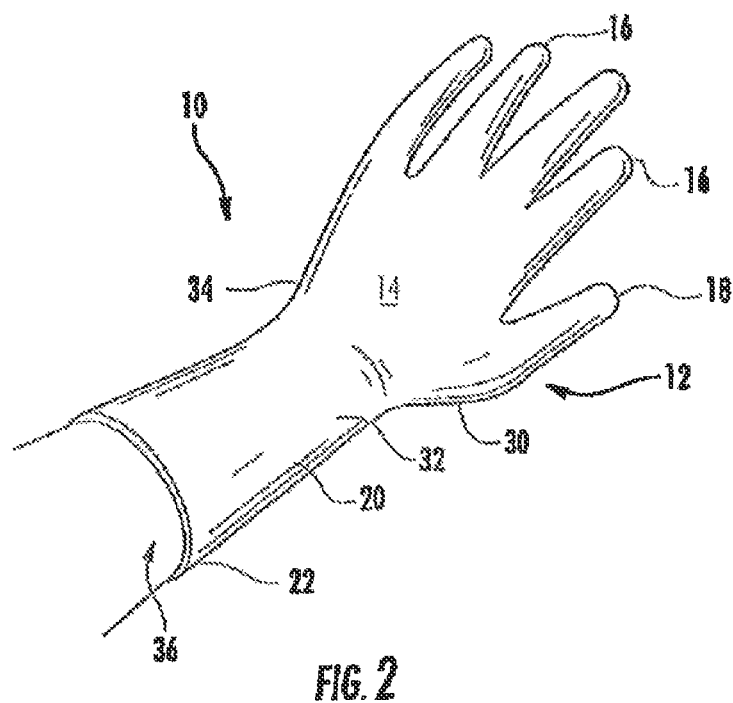
FIG. 2 is a perspective view of a glove made in accordance with the present disclosure.

Referring to FIG. 2, a glove 10 made in accordance with the present disclosure is shown. Although the figures and the following description generally refer to gloves, it should be understood that the teachings of the present disclosure can be used to produce other elastic articles. For instance, other elastic articles that may be made in accordance with the present disclosure include catheters, balloons, tubing, and the like.

As shown in FIG. 2, the glove 10 is generally in the shape of a hand. Of particular advantage, gloves made in accordance with the present disclosure have form-fitting properties in that the glove tightly conforms to the hand of a wearer and is elastic allowing the hand to freely move inside the glove.

The glove 10 includes a palm region 12, a back region 14, a plurality of finger regions 16, and a thumb region 18. The glove 10 can further include a wrist portion 20 terminating at a cuff 22.

In accordance with the present disclosure, the glove 10 includes a first hand-shaped panel 30 that is welded to a second hand-shaped panel 32. As will be described in greater detail below, the first panel 30 is welded to the second panel 32 to form a seam 34. The first and second panels are welded together about their peripheries in a manner that forms an opening 36 for receiving a hand. The seam 34 may not be visible after the panels are welded together.

Figure 3:
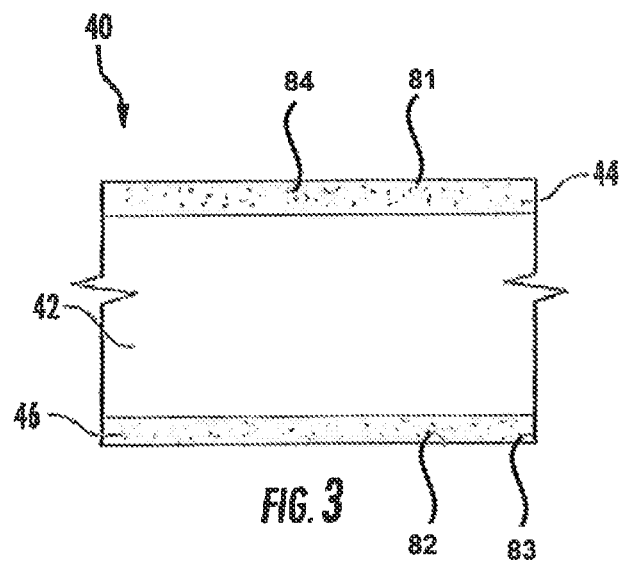
FIG. 3 and FIG. 3B are cross-sectional views of multi-layer films that may be used in accordance with the present disclosure.

As described above, the glove 10 as shown in FIG. 2 is formed from a multi-layered film. One embodiment of a multi-layered film that may be used in accordance with the present disclosure is shown in FIG. 3. In the embodiment illustrated, the multi-layer film 40 includes three layers: a middle layer 42 positioned in between a first outer layer 44 and a second outer layer 46. It should be understood that the multi-layered film may include more than three layers by including a plurality of middle layers.

When the multi-layer film 40 as shown in FIG. 3 is used to form the glove 10 illustrated in FIG. 2, the first layer 44 may comprise the exterior surface of the glove, while the second layer 46 may comprise the interior surface of the glove, which is the surface of the glove adjacent to the hand of the wearer. In accordance with the present disclosure, each of the different layers within the film 40 can have a different composition and different properties depending upon the particular application. The middle layer 42, for instance, may comprise the primary elastic matrix for the glove. The first layer 44, on the other hand, may be formulated so as to enhance grip, reduce blocking, may include another property or characteristic that may be important depending upon the particular application. The second layer 46, on the other hand, may be formulated so as to improve the donnability of the glove and/or be formulated to promote the formation of a weld (such as by including a weld-enhancing additive). For example, the second layer 46 may be configured to allow a person to easily place the glove over one's hand.

In general, all of the layers of the multi-layer film 40 can contain a thermoplastic elastomer. All of the layers can contain the same thermoplastic elastomer. In some embodiments, however, each layer may contain a different thermoplastic elastomer.

Thermoplastic elastomers that may be used to produce the multi-layer film 40 can vary depending upon the particular application. In one embodiment, the thermoplastic elastomer has desired elastic properties. For instance, the multi-layer film can be made from thermoplastic elastomers such that the film can be stretched at least about 300%, such as at least about 400%, such as at least about 500%, such as at least about 600% without breaking or ripping.

In one embodiment, the multi-layer film may also have hysteresis characteristics that are similar or better than materials used in the past to produce dip-formed gloves. For example, after being stretched 250% after one cycle, the film may have a hysteresis loss of less than about 100%, such as less than about 90%, such as less than about 80%, such as less than about 75%. In some embodiments, the film may have a low hysteresis loss such as less than about 60%, such as less than about 50%, such as less than about 40%, such as less than about 30%, such as less than about 20%, such as less than about 10%. After one cycle, the film may also have a percent set of less than about 95%, such as less than about 90%, such as less than about 85%, such as less than about 80%. Similar to hysteresis loss, the film may also have a percent set of less than about 70%, such as less than about 60%, such as less than about 50%, such as less than about 40%, such as less than about 30%, such as less than about 20%, such as less than about 10%. In general, the hysteresis loss and the percent set are greater than zero percent. As used herein, hysteresis loss and percent set are measured in the machine direction unless otherwise stated. Hysteresis loss and percent set can be measured at different thicknesses.

Of particular advantage, the multi-layer film can have the above hysteresis characteristics while also possessing excellent strength characteristics. In fact, the multi-layer film of the present disclosure may have strength characteristics better than many materials used to form dip-formed gloves, such as nitrile polymers and natural latex polymers. For example, the multi-layer film may have a breaking strength (after three cycles of 250% elongation) of greater than about 10 N, such as greater than about 14 N, such as even greater than about 20 N. In general, the break strength is less than about 50 N.

Examples of thermoplastic elastomers that may be used to form the multi-layer film 40 include polyurethanes, polyolefins, styrenic block copolymers, polyether amides, and polyesters.

For example, in one embodiment, the multi-layer film may be made from a thermoplastic polyurethane elastomer. Thermoplastic polyurethane elastomers generally include a soft segment and a hard segment. The soft segment can be derived from a long-chain dial while the hard segment may be derived from a diisocyanate. The hard segment may also be produced using chain extenders. For example, in one embodiment, a long-chain diol is reacted with a diisocyanate to produce a polyurethane prepolymer having isocyanate end groups. The prepolymer is then reacted with a chain extender, such as low molecular weight hydroxyl and amine terminated compounds. Suitable chain extenders include aliphatic diols, such as ethylene glycol, 1,4-butane dial, 1,6-hexane diol, and neopentyl glycol.

In one particular embodiment, the thermoplastic polyurethane elastomer may be polyether-based or polyester-based. In an alternative embodiment, the thermoplastic polyurethane elastomer may be formed with a polymethylene-based soft segment, such as a polytetramethylene glycol-based soft segment.

In one embodiment, a thermoplastic polyurethane elastomer is used that has a density of from about 1.0 g/cc to about 1.2 g/cc. For example, in one embodiment, the polyurethane elastomer is polyether-based and has a density of from about 1.04 g/cc to about 1.07 g/cc. In an alternative embodiment, the polyurethane elastomer includes polymethylene-based soft segments and has a density of from about 1.12 g/cc to about 1.15 g/cc.

The polyurethane elastomer can have a Shore A hardness (according to ASTM Test D2240) of generally greater than about 75 and generally less than about 95. In one embodiment, for instance, the polyurethane elastomer may have a Shore A hardness of greater than about 78, such as greater than about 80, such as from about 79 to about 82. In an alternative embodiment, the polyurethane elastomer may have a Shore A hardness of from about 75 to about 94, such as from about 86 to about 94.

The thermoplastic elastomer can have a melting range of from about 190° C. to about 225° C. In one embodiment, for instance, the melting range can be from about 195° C. to about 205° C. In an alternative embodiment, the melting range can be from about 200° C. to about 225° C.

The polyurethane elastomer can have a modulus at 100% elongation of generally greater than about 3 MPa, such as greater than about 5 MPa, such as greater than about 6 MPa, such as even greater than about 10 MPa. In general, the modulus at 100% elongation is less than about 20 MPa, such as less than about 15 MPa.

In addition to thermoplastic polyurethane elastomers, the film of the present disclosure may also be made from polyolefin elastomers, which includes herein polyolefin plastomers. The thermoplastic polyolefin may comprise, for instance, a polypropylene polymer, a polyethylene polymer, a polybutylene polymer or a copolymer thereof.

In one particular embodiment, a polyolefin plastomer is used that comprises an alpha olefin copolymer, particularly an alpha olefin polyethylene copolymer. Suitable alpha-olefins may be linear or branched (e.g., one or more $C_1$-$C_3$ alkyl branches, or an aryl group). Specific examples include ethylene, 1-butene; 3-methyl-1-butene; 3,3-dimethyl-1-butene; 1-pentene; 1-pentene with one or more methyl, ethyl or propyl substituents; 1-hexene with one or more methyl, ethyl or propyl substituents; 1-heptene with one or more methyl, ethyl or propyl substituents; 1-octene with one or more methyl, ethyl or propyl substituents; 1-nonene with one or more methyl, ethyl or propyl substituents; ethyl, methyl or dimethyl-substituted 1-decene; 1-dodecene; and styrene. Particularly desired alpha-olefin comonomers are ethylene, 1-butene, 1-hexene and 1-octene. The ethylene content of such copolymers may be from about 60 mole % to about 99.5 wt. %, in some embodiments from about 80 mole % to about 99 mole %, and in some embodiments, from about 85 mole % to about 98 mole %. The alpha-olefin content may likewise range from about 0.5 mole % to about 40 mole %, in some embodiments from about 1 mole % to about 20 mole %, and in some embodiments, from about 2 mole % to about 15 mole %. The distribution of the alpha-olefin comonomer is typically random and uniform among the differing molecular weight fractions forming the ethylene copolymer.

Density of the thermoplastic polyolefin may generally be less than about 0.95 g/cc, such as less than about 0.91 g/cc. The density of the polyolefin is generally greater than about 0.8 g/cc, such as greater than about 0.85 g/cc, such as greater than about 0.88 g/cc. In one embodiment, for instance, a thermoplastic polyolefin is used that has a density of 0.885 g/cc or greater, such as from about 0.885 g/cc to about 0.91 g/cc.

The thermoplastic polyolefin may have a melt flow index when measured according to ASTM Test D1238 at 190° C. and at a load of 2.16 kg of from about 1 g/10 mins. to about 40 g/10 mins., such as from about 5 g/10 mins. to about 35 g/10 mins. At 230° C. and at a load of 2.16 kg, the melt flow index can be from about 1 g/10 min to about 350 g/10 min, such as from about 1 g/10 min to about 100 g/10 min.

In another embodiment, the thermoplastic polymer contained in the multi-layer film may comprise a block copolymer. For example, the elastomer may be a substantially amorphous block copolymer having at least two blocks of a monoalkenyl arene polymer separated by at least one block of a saturated conjugated diene polymer. The monoalkenyl arene blocks may include styrene and its analogues and homologues, such as o-methyl styrene; p-methyl styrene; p-tert-butyl styrene; 1,3 dimethyl styrene p-methyl styrene; etc., as well as other monoalkenyl polycyclic aromatic compounds, such as vinyl naphthalene; vinyl anthrycene; and so forth. Preferred monoalkenyl arenes are styrene and p-methyl styrene. The conjugated diene blocks may include homopolymers of conjugated diene monomers, copolymers of two or more conjugated dienes, and copolymers of one or more of the dienes with another monomer in which the blocks are predominantly conjugated diene units. Preferably, the conjugated dienes contain from 4 to 8 carbon atoms, such as 1,3 butadiene (butadiene); 2-methyl-1,3 butadiene; isoprene; 2,3 dimethyl-1,3 butadiene; 1,3 pentadiene (piperylene); 1,3 hexadiene; and so forth. The amount of monoalkenyl arene (e.g., polystyrene) blocks may vary, but typically constitute from about 8 wt. % to about 55 wt. %, in some embodiments from about 10 wt. % to about 35 wt. %, and in some embodiments, from about 25 wt. % to about 35 wt. % of the copolymer. Suitable block copolymers may contain monoalkenyl arene endblocks having a number average molecular weight from about 5,000 to about 35,000 and saturated conjugated diene midblocks having a number average molecular weight from about 20,000 to about 170,000. The total number average molecular weight of the block polymer may be from about 30,000 to about 250,000.

Particularly suitable elastomers are available from Kraton Polymers LLC of Houston, Tex. under the trade name KRATON®. KRATON® polymers include styrene-diene block copolymers, such as styrene-butadiene, styrene-isoprene, styrene-butadiene-styrene, and styrene-isoprene-styrene. KRATON® polymers also include styrene-olefin block copolymers formed by selective hydrogenation of styrene-diene block copolymers. Examples of such styrene-olefin block copolymers include styrene-(ethylene-butylene), styrene-(ethylene-propylene), styrene-(ethylene-butylene)-styrene, styrene-(ethylene-propylene)-styrene, styrene-(ethylene-butylene)-styrene-(ethylene-butylene), styrene-(ethylene-propylene)-styrene-(ethylene-propylene), and styrene-ethylene-(ethylene-propylene)-styrene. These block copolymers may have a linear, radial or star-shaped molecular configuration. Specific KRATON® block copolymers include those sold under the brand names G 1652, G 1657, G 1730, MD6673, and MD6937. Various suitable styrenic block copolymers are described in U.S. Pat. Nos. 4,663,220, 4,323,534, 4,834,738, 5,093,422 and 5,304,599, which are hereby incorporated in their entirety by reference thereto for all purposes. Other commercially available block copolymers include the S-EP-S elastomeric copolymers available from Kuraray Company, Ltd. of Okayama, Japan, under the trade designation SEPTON®. Still other suitable copolymers include the S-I-S and S-B-S elastomeric copolymers available from Dexco Polymers of Houston, Tex. under the trade designation VECTOR®. Also suitable are polymers composed of an A-B-A-B tetrablock copolymer, such as discussed in U.S. Pat. No. 5,332,613 to Taylor, et al., which is incorporated herein in its entirety by reference thereto for all purposes. An example of such a tetrablock copolymer is a styrene-poly(ethylene-propylene)-styrene-poly(ethylene-propylene) ("S-EP-S-EP") block copolymer.

Various thermoplastic elastomers that may be incorporated into elastic articles in accordance with the present disclosure include ARNITEL polymers available from DSM Engineering Plastics, VISTAMAXX polymers available from ExxonMobil Chemical Company, AFFINITY polymers available from The Dow Chemical Company, SANTOPRENE polymers available from ExxonMobil Chemical Company, PEARLTHANE polymers available from Merquinsa, PELLETHANE polymers available from Lubrizol, PEBAX polymers available from Arkema Technical Polymers, ESTANE polymers available from Lubrizol, INFUSE polymers available from The Dow Chemical Company, and the like.

Multi-layer films used in accordance with the present disclosure can generally have a thickness of less than about 10 mils. For instance, the multi-layer film may have a thickness of from about 0.5 mils to about 8 mils, such as from about 1 mil to about 6 mils. As shown in FIG. 3, in some embodiments, the middle layer 42 may have a thickness greater than the outer layers 44 and 46. The one or more middle layers 42, for instance, may comprise the primary matrix of the glove providing the glove with its elastic properties, while the outer layers are primarily used as functional layers. In this regard, each outer layer 44 and 46 may comprise from about 5% to about 25% of the thickness of the film, such as from about 5% to about 10% of the total thickness of the film.

As described above, each layer of the film may contain the same thermoplastic polymer or may be comprised of a different polymer or different polymer blend. In one embodiment, the multi-layer film is produced through a coextrusion process. In this regard, the polymers used to produce each layer should be compatible for such processes. The multi-layer film may be produced through a cast process or a blown process.

As described above, the second layer 46 of the multi-layer film 40 may, in one embodiment, comprise the donning layer of the glove 10 as shown in FIG. 2. In this regard, in one embodiment, in addition to a thermoplastic polymer, the second layer 46 may contain a friction-reducing additive 82 such as filler particles 83 as shown in FIG. 3 for facilitating donning of the glove. The friction-reducing additive may vary depending upon the particular application and the desired result. In one embodiment, a friction-reducing additive is present in the second layer 46 such that the inside layer of the glove has a static coefficient of friction of less than about 0.3, such as less than about 0.25, such as less than about 0.2 (when measured according to ASTM Test D1894-11).

In one embodiment, the friction-reducing additive may comprise particles incorporated into the second film layer 46. The particles may comprise, for instance, filler particles, such as aluminum oxide particles or silicon dioxide particles. In addition to the above particles, various other filler particles may be used as the friction-reducing additive. For instance, other particles that may be used include calcium carbonate particles, mica, and the like. The particles can be incorporated into the outer layer in a manner that disrupts the surface of the outer layer for reducing friction. The particles can be completely embedded within the outer layer 46.

The size of the particles and the amount of particles contained in the outer film layer 46 can vary depending upon the particular application. In general, the particles are incorporated into the second film layer in an amount from about 15% to about 50% by weight, such as in an amount from about 20% to about 40% by weight. The particles generally have a size of less than about 15 microns, such as less than about 10 microns. The particles generally have a size greater than 1 micron, such as greater than about 2 microns.

In an alternative embodiment, the friction-reducing additive may comprise nanoparticles, such as particles having a particle size of less than 1 micron, such as less than 0.5 microns, such as less than about 0.1 microns. Such particles may be incorporated into the film layer in relatively small amounts, such as in amounts from about 0.1% to about 10% by weight.

In another embodiment of the present disclosure, the friction-reducing additive may comprise a fluorocarbon compound, silicone or a fatty acid (which includes fatty acid derivatives) which may be combined with the polymer used to form the second layer or may be applied to the second surface 46. As used herein, the term "silicone" generally refers to a broad family of synthetic polymers that have a repeating silicon-oxygen backbone, including, but not limited to, polydimethylsiloxane and polysiloxanes having hydrogen-bonding functional groups selected from the group consisting of amino, carboxyl, hydroxyl, ether, polyether, aldehyde, ketone, amide, ester, and thiol groups.

Generally, any silicone capable of enhancing the donning characteristics of the glove may be used. In some embodiments, polydimethylsiloxane and/or modified polysiloxanes may be used as the silicone component. For instance, some suitable modified polysiloxanes that may be used include, but are not limited to, phenyl-modified polysiloxanes, vinyl-modified polysiloxanes, methyl-modified polysiloxanes, fluoro-modified polysiloxanes, alkyl-modified polysiloxanes, alkoxy-modified polysiloxanes, amino-modified polysiloxanes, and combinations thereof.

Some suitable phenyl-modified polysiloxanes include, but are not limited to, dimethyldiphenylpolysiloxane copolymers; dimethyl, methylphenylpolysiloxane copolymers; polymethylphenylsiloxane; and methylphenyl, dimethylsiloxane copolymers.

As indicated above, fluoro-modified polysiloxanes may also be used in the present invention. For instance, one suitable fluoro-modified polysiloxane that may be used is a trifluoropropyl modified polysiloxane, such as a trifluoropropylsiloxane modified dimethylpolysiloxane. A trifluoropropylsiloxane modified dimethylpolysiloxane may be synthesized by reacting methyl, 3,3,3 trifluoropropylsiloxane with dimethylsiloxane.

Besides the above-mentioned modified polysiloxanes, other modified polysiloxanes may also be utilized. For instance, some suitable vinyl-modified polysiloxanes include, but are not limited to, vinyldimethyl terminated polydimethylsiloxanes; vinylmethyl, dimethylpolysiloxane copolymers; vinyldimethyl terminated vinylmethyl, dimethylpolysiloxane copolymers; divinylmethyl terminated polydimethylsiloxanes; and vinylphenylmethyl terminated polydimethylsiloxanes. Further, some methyl-modified polysiloxanes that may be used include, but are not limited to, dimethylhydro terminated polydimethylsiloxanes; methylhydro, dimethylpolysiloxane copolymers; methylhydro terminated methyloctyl siloxane copolymers; and methylhydro, phenylmethyl siloxane copolymers. In addition, some examples of amino-modified polysiloxanes include, but are not limited to, polymethyl(3-aminopropyl)-siloxane and polymethyl[3-(2-aminoethyl)aminopropyl]-siloxane.

In one embodiment, the second layer 46 is made from an elastomeric polymer that is different than the other layers of the multi-layer film. For example, the second layer 46 may be made from a thermoplastic polymer that has a Shore A hardness that is greater than the Shore A hardness of the polymers used to form the other layers. For example, the Shore A hardness of the second layer 46 may be at least about 2% greater, such as at least about 5% greater, such as at least about 10% greater than the Shore A hardness of the middle layer. In one particular embodiment, for instance, the second layer 46 and the middle layer 42 may be made from a thermoplastic polyurethane elastomer wherein the thermoplastic polyurethane elastomer used to produce the second layer 46 has a Shore A hardness greater than the thermoplastic polyurethane elastomer used to form the middle layer 42.

In addition to formulating the second layer 46 to facilitate donning, the first layer 44 of the multi-layer film 40 may also be formulated so as to enhance gripping or provide other benefits, such as reduce blocking or the tendency of the gloves to stick together. For instance, in one embodiment, a gripping or anti-blocking agent 84, such as particles 81 as shown in FIG. 3, such as metal oxide particles, may be incorporated into the first layer 44 so as to increase the coefficient of friction of the film surface. In one embodiment, for instance, the first outer layer 44 may include colloidal silica particles that remain partially exposed on the outside surface of the film.

In one embodiment, the first layer 44 may contain any of the particles described above that may be contained in the second layer 46, except in lower amounts. For example, particles may be incorporated into the first layer 44 in an amount from about 2% to about 15% by weight, such as in an amount from about 5% to about 12% by weight. The particles are added to the first layer 44 in lower amounts that may improve the gripping properties of the glove and/or reduce blocking.

In one embodiment, the particles incorporated into the first layer 44 may comprise electrically conductive particles. In this manner, the particles may allow static charges to be dissipated where anti-static performance is desired. For instance, in one embodiment, the particles may comprise colloidal silica particles that are coated so as to be rendered electrically conductive. For example, one embodiment of an electrically conductive surface treatment comprises aluminum chlorohydrate. In other embodiments, the particles may be coated with a layer of a metal.

In an alternative embodiment, other anti-static agents may be incorporated into the first layer 44 of the multi-layer film. The anti-static agent may comprise a resin that is combined with the thermoplastic polymer.

In one embodiment, one or more coloring agents may be incorporated into the multi-layer film. The coloring agents may comprise dyes, pigments, particles, or any other material capable of imparting color to one or more of the layers. A coloring agent, for instance, may be incorporated into a single layer or into all of the layers of the multi-layer film. In one particular embodiment, for instance, a coloring agent is only added to the first layer 44 of the film.

In other embodiments, different coloring agents may be added to different layers of the multi-layer film. For instance, in one embodiment, a first coloring agent may be incorporated into the first layer 44 while a second coloring agent may be incorporated into the second layer 46. The different coloring agents may combine to produce a unique look or effect.

In one embodiment, for instance, the second layer 46 contains a coloring agent that makes the layer a solid color and opaque. For instance, in one embodiment, white pigment particles may be incorporated into the second layer for producing a white-colored layer that is opaque. The pigment particles, for instance, may comprise titanium dioxide particles. The titanium dioxide particles may be incorporated into the second layer in an amount from about 1% to about 10% by weight. A different coloring agent may then be incorporated into the first layer 44 that changes the color of the first layer while rendering the first layer translucent. The first layer, for instance, may include a coloring agent that renders the first layer any suitable color, such as purple, red, blue, green or the like.

Combining an opaque, white second layer in combination with a translucent first layer provides various advantages and benefits. For instance, the combination of the translucent layer with the opaque layer may provide for depth enhancement. The white opaque layer may also reflect light and enhance the color of the translucent outer layer.

In addition to the first layer, the middle layer and the second layer as shown in FIG. 3, the multi-layer film 40 may also include various other surface treatments as desired. The surface treatment may be on the donning side of the glove or may be on the exterior surface of the glove. In one embodiment, skin layers may be applied to the first layer and/or the second layer.

Once the multi-layer film 40 as shown in FIG. 3 has been formed, the film can then be used to form an elastic article, such as a glove. In one particular embodiment, a glove or other elastic article can be formed without laminating any further materials to the multi-layer film. Thus, the glove can be made from a non-laminated film.

Figure 3B:
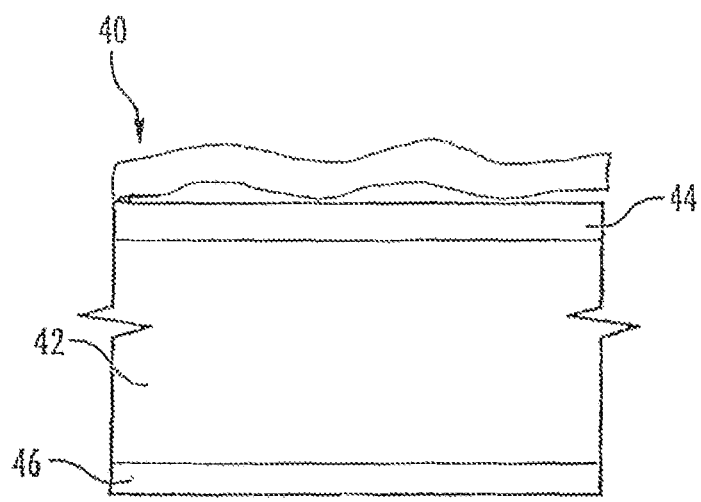

In an alternative embodiment, other materials may be laminated to the film prior to forming the elastic article. For instance, in one embodiment, an extensible fabric can be laminated to one side of the multi-layer film prior to forming the elastic article as shown in FIG. 3B. The extensible nonwoven may comprise, for instance, a nonwoven web to provide the elastic article with a cloth-like feel.

Nonwoven webs that may be laminated to the film include meltblown webs, spunbond webs, bonded carded webs, and the like. In one embodiment, a spunbond/meltblown/spunbond laminate or a spunbond/meltblown laminate may be laminated to the multi-layer film. In still another embodiment, a hydroentangled web may be laminated to the film. The hydroentangled web may comprise a spunbond web hydroentangled with pulp fibers. The fabric laminated to the film may be extensible and non-elastic or extensible and elastic. The fabric can be laminated to the film using an adhesive or can be thermally bonded to the film.

In order to form an elastic article, such as the glove 10 shown in FIG. 2, two plies of the multi-layer film can be welded together. The two films can be bonded together, for instance, using thermal bonding, ultrasonic bonding, or the like.

Figure 1B:
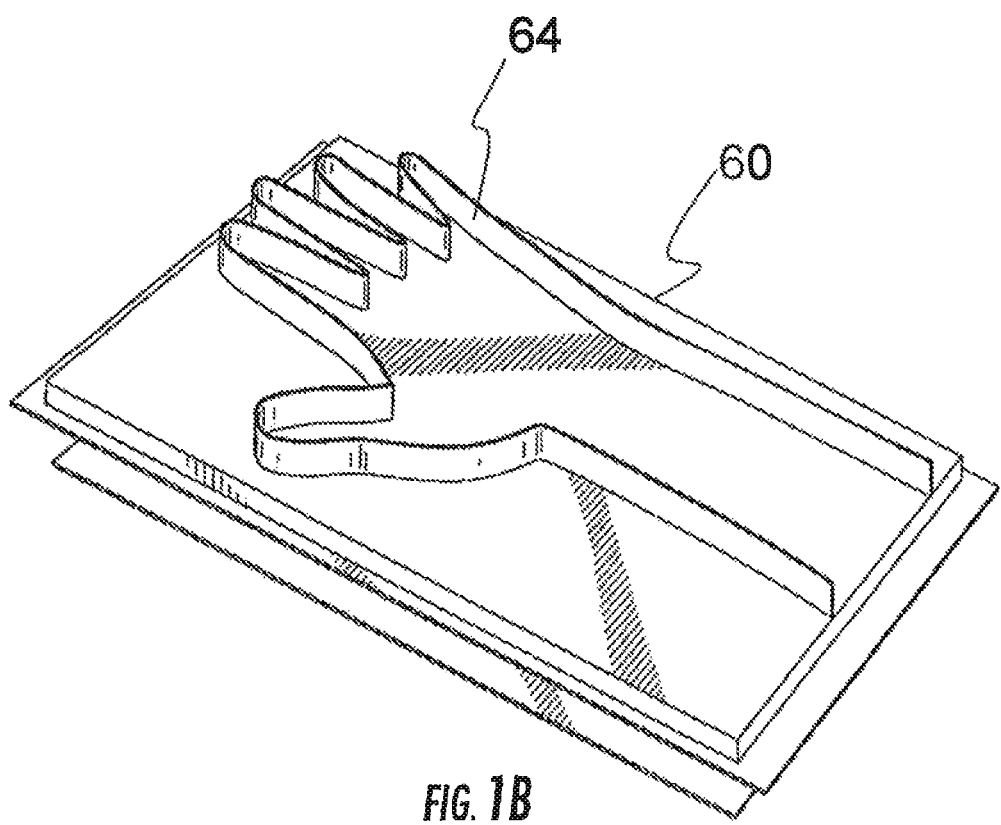
FIG. 1B is a perspective view of a hand-shaped wire that may be used in the apparatus illustrated in FIG. 1A.

Referring to FIGS. 1A and 1B, for instance, one embodiment of a system for producing welded gloves from the multi-layer film is illustrated. As shown in FIG. 1A, the system 50 includes a plurality of roll letoffs 52 and 54 for feeding multiple plies of the multi-layer film into the process. In the embodiment illustrated in FIG. 1A, the system 50 includes a first roll letoff 52 and a second roll letoff 54 that are each configured to support and unwind a spirally wound roll of the multi-layer film of the present disclosure. In other embodiments, the system 50 may include more than two roll letoffs for feeding more than two plies of the film into the process. In one embodiment, for instance, the thumb portion of a glove may be formed separately from the finger portions. In this embodiment, a third roll letoff may be used to create the thumb portion which is then welded to the glove separately.

The glove-making system 50 as shown in FIG. 1A generally includes a frame 56 that supports the components including the roll letoffs 52 and 54.

When forming gloves using the system 50 as shown in FIG. 1A, at least two plies of the multi-layer film are unwound from the roll letoffs 52 and 54 and fed to at least one die device 58. The die device 58, which may be hydraulically or pneumatically operated, includes a pair of opposing platens 60 and 62. The platens 60 and 62 come together and form a glove from the two plies of film while the plies of film are in a superimposed relationship.

For example, in one embodiment, the top platen 60 as shown in FIG. 1B may include a welding device 64 which delivers energy to the two plies of film. For instance, the welding device 64 may comprise a heated wire or may comprise an ultrasonic device that welds the two plies of film together in the shape of a glove while also simultaneously cutting the glove from the plies of film. The formed glove is then collected while the film scrap is fed downstream and reused as desired.

Of particular advantage, as shown in FIG. 1B, a welding device 64 may be used that produces a glove with form-fitting properties. In this regard, the resulting glove can fit tightly and snugly on one's hand as opposed to being "baggy".

Of particular advantage, gloves formed in accordance with the present disclosure can be produced so as to have form-fitting properties. In particular, thermoplastic elastomers (including plastomers) can be selected in producing the multi-layer film such that the resulting glove has excellent elastic properties in combination with excellent tactile properties.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed:

1. A glove comprising:
a first hand-shaped panel defining a periphery;
a second hand-shaped panel also defining a periphery, the second hand-shaped panel having been welded to the first hand-shaped panel about the peripheries of the hand-shaped panels in a manner that forms a hollow opening for receiving a hand, the glove including a seam where the first hand-shaped panel has been welded to the second hand-shaped panel, the hand-shaped panels each being comprised of a non-laminated, elastic multi-layer film having three layers, the multi-layer film comprising a middle layer positioned in between a first layer and a second layer wherein the middle layer has a thickness that is greater than a thickness of the first layer and the thickness of the middle layer is greater than a thickness of the second layer, the first layer of each hand-shaped panel forming an exterior surface of the glove, the second layer of each hand-shaped panel forming an interior surface of the glove, and wherein the non-laminated, elastic multi-layer film is made from a thermoplastic elastomer such that the middle layer, the first layer, and the second layer are all made from the same thermoplastic elastomer, and wherein although each layer contains the same thermoplastic elastomer, each layer of the multi-layer film includes a different composition of ingredients, the second layer being different than the middle layer by the second layer containing a friction-reducing additive, the friction-reducing additive comprising filler particles present in the second layer sufficient so that the second layer has a static coefficient of friction of 0.3 or less, the first layer being different than the middle layer by the first layer containing a gripping or anti-blocking agent, the first layer containing the thermoplastic elastomer combined with the gripping or anti-blocking agent, the second layer comprising the thermoplastic elastomer combined with the friction-reducing additive comprising the filler particles, the multi-layer film having a total thickness of 8 mils or less.

2. A glove as defined in claim 1, wherein the thermoplastic elastomer that is used to form the first layer, the middle layer and the second layer comprises a thermoplastic polyurethane elastomer.

3. A glove as defined in claim 2, wherein the thermoplastic polyurethane elastomer includes polymethylene-based soft segments.

4. a glove as defined in claim 2, wherein the thermoplastic polyurethane elastomer is polyether-based.

5. a glove as defined in claim 2, wherein the thermoplastic polyurethane elastomer is polyester-based.

6. A glove as defined in claim 2, wherein the thermoplastic polyurethane elastomer has a density of from 1.0 to 1.2 grams/centimeter$^3$ and has a Shore A hardness of from 86 to 94.

7. A glove as defined in claim 1, wherein the total thickness of the multi-layer film is 6 mils or less.

8. A glove as defined in claim 1, wherein the friction-reducing additive is contained in the second layer in an amount from 15% to 50% by weight.

9. A glove as defined in claim 1, wherein the friction-reducing additive contained in the second layer comprises particles, the particles being present in the second layer in an amount from 20% to 40% by weight and wherein the particles have a particle size of from 2 microns to 10 microns.

10. A glove as defined in claim 1, wherein the gripping or anti-blocking agent is present in the first layer in an amount from 5% to 15% by weight.

11. A glove as defined in claim 10, wherein the gripping or anti-blocking agent comprises filler particles.

12. A glove as defined in claim 1, wherein each layer of the multi-layer film has a hysteresis loss after being stretched to 250% elongation of 100% or less and has a percent set of 95% or less.

13. A glove as defined in claim 1, wherein the glove contains a coloring agent, the coloring agent being located in the first layer of the multi-layer film.

14. A glove as defined in claim 1, wherein the second layer contains a coloring agent comprising white pigment particles.

15. A glove as defined in claim 14, wherein the first layer contains a second coloring agent, the first layer being translucent.

16. A glove as defined in claim 1, wherein the first layer contains an antistatic agent.

17. A glove as defined in claim 1, wherein the friction-reducing additive of each of the first and second layers comprises oxide particles.

* * * * *